(12) United States Patent
Schubert

(10) Patent No.: US 8,303,610 B2
(45) Date of Patent: Nov. 6, 2012

(54) DEVICE FOR THE PRODUCTION OF ANASTOMOSES BETWEEN HOLLOW ORGANS

(75) Inventor: Heinrich Schubert, Innsbruck (AT)

(73) Assignee: Erbe Elektromedizin GmbH, Tübingen (DE)

(*) Notice: Subject to any disclaimer, the term of this patent is extended or adjusted under 35 U.S.C. 154(b) by 1289 days.

(21) Appl. No.: 10/502,239

(22) PCT Filed: Jan. 24, 2003

(86) PCT No.: PCT/EP03/00744
§ 371 (c)(1),
(2), (4) Date: Jul. 22, 2004

(87) PCT Pub. No.: WO03/061487
PCT Pub. Date: Jul. 31, 2003

(65) Prior Publication Data
US 2005/0055022 A1 Mar. 10, 2005

(30) Foreign Application Priority Data
Jan. 25, 2002 (AT) .................................. A 123/2002

(51) Int. Cl.
*A61B 17/11* (2006.01)
(52) U.S. Cl. ...................................... 606/153; 606/151
(58) Field of Classification Search .................. 606/151, 606/153–156, 32–34, 37
See application file for complete search history.

(56) References Cited

U.S. PATENT DOCUMENTS

| | | | | |
|---|---|---|---|---|
| 3,357,432 A | * | 12/1967 | Sparks | 606/151 |
| 3,683,926 A | | 8/1972 | Suzuki | |
| 3,774,615 A | * | 11/1973 | Lim et al. | 606/153 |
| 4,470,415 A | * | 9/1984 | Wozniak | 606/149 |
| 4,873,975 A | * | 10/1989 | Walsh et al. | 606/153 |
| 4,892,098 A | | 1/1990 | Sauer | |
| 5,188,638 A | * | 2/1993 | Tzakis | 606/153 |
| 5,861,168 A | * | 1/1999 | Cooke et al. | 424/424 |
| 6,190,397 B1 | * | 2/2001 | Spence et al. | 606/153 |
| 6,241,743 B1 | * | 6/2001 | Levin et al. | 606/153 |
| 6,293,955 B1 | * | 9/2001 | Houser et al. | 606/153 |

FOREIGN PATENT DOCUMENTS

| | | |
|---|---|---|
| JP | 2001017438 | 1/2001 |
| WO | WO 98/38935 | 9/1998 |

* cited by examiner

*Primary Examiner* — Darwin Erezo
(74) *Attorney, Agent, or Firm* — Dickstein Shapiro LLP

(57) ABSTRACT

A device for producing anastomoses between hollow organs. The device includes an inner sleeve mounted around the end of the first hollow organ and an outer sleeve mounted around the end of the second hollow organ, the end being arranged over the end of the first hollow organ, which is turned inside out over the inner sleeve. The inner sleeve and outer sleeve are separable. In order to obtain a secure and durable anastomosis that is easy to carry out, the inner sleeve and outer sleeve comprise electricity-conducting materials, for example in the form of contact surfaces that can be connected to an external power or voltage to electrocoagulate the hollow organs that are to be joined.

26 Claims, 4 Drawing Sheets

DEVICE FOR THE PRODUCTION OF ANASTOMOSES BETWEEN HOLLOW ORGANS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to a device for the production of anastomoses between hollow organs, with an inner sleeve to be mounted around the end of the first hollow organ and with an outer sleeve to be mounted around the end of the second hollow organ after the latter end has been arranged over the end of the first hollow organ, which has been turned inside out over the inner sleeve, the inner and outer sleeves being made separable so that they can be removed after anastomosis formation has been completed.

BACKGROUND OF THE INVENTION

The term "hollow organs" denotes, for example, blood vessels as well as the structures through which urine flows and the hollow organs of the digestive tract etc., and the need to connect such organs arises very often in surgery. In all such cases a distinction is made between end-to-end anastomoses, in which two ends of two hollow organs are connected to one another, and end-to-side anastomoses, in which the end of one hollow organ is put into communication with a second organ at the side of the latter.

For connecting hollow organs the predominant techniques involve stitching, such that a plurality of sutures create the junction. Apart from the great surgical effort involved here, in particular in the case of small vessels, the region of the sutures is frequently affected by complications such as thromboses, in the case of blood vessels.

In addition to the stitching techniques, there also exist adhesive techniques, for instance employing fibrin adhesives, which allow anastomoses to be formed more rapidly than is the case with sutures, and furthermore the resulting connections are more elastic. It is disadvantageous here that many adhesives are thrombogenic and toxic, and hence are not to be recommended, in particular for vascular anastomoses.

In addition to the above-mentioned stitching and adhesive techniques, clamping techniques are used in which specially shaped clamps create the vessel connections; these can be attached in less time than it takes to stitch conventional sutures. To assist the production of anastomoses, since the beginning of the 20th Century various accessories such as rings, "cuffs" or stents have been used, by means of which secure, rapid and reliable connections can be created. The disadvantage here is that these accessories ordinarily remain in place after the organs have been connected, and then can elicit rejection responses or, in the case of vascular anastomoses, can increase the risk of thromboses. To avoid these problems it has been specified that these accessories be made of materials that disintegrate after a certain time, as described for instance in the document DE 44 17 528 A1. The document EP 0 554 990 B1 describes an apparatus of the kind cited above for constructing anastomoses in which the hollow organs are connected by means of sutures and clamps. The sleeves used to promote anastomosis formation can be made separable, so that they can be removed after anastomosis formation has been completed. Subsequently, however, the sutures and clamps still remain in the hollow organ, where they can increase the risk of thrombosis if the anastomosed structures are vessels.

Laser energy can also be employed to connect biological tissue: when it is applied to hollow organs that are to be connected, the resultant heating causes the tissue of the organs to become fused. Anastomoses thus created by laser exhibit a less pronounced foreign-body reaction. With respect to thrombogenesis, however, no advantage of this approach has yet been demonstrated. Furthermore, the temperatures produced by a laser can also cause destruction of the tissue. An apparatus for fusing biological tissue by means of laser energy is described, for example in the document EP 480 293 A1.

In addition to the production of heat by means of lasers, methods also exist in which local temperature elevations for the purpose of fusing biological tissue are produced by means of electrical current. If the tissue temperature remains below a value of about 100° C., the result is that the substance of the cells coagulates and their protein structures stick to one another in a disorderly manner, so that tissues can become fused. This kind of seamless method of producing vessel anastomosis has been implemented, for example, by means of wire rings disposed around the ends of the vessels, with the supplementary use of fibrin adhesives (E. Wintermantel: The thermic vascular anastomosis (TVA). A new nonsuture method. I. History, Instruments and microsurgical technique; Acta Neurochir. 1981; 56 (1-2): 5-24). The tissue coagulation was produced by imposing several brief current pulses. The wire rings through which the current was introduced, however, were left in place at the anastomosis site. A device for the electrothermal implementation of tissue connections has also been described in the document WO 98/38935 A1.

Another device for the suture-free production of end-to-end anastomoses is described in the document WO 99/63910 A1; here the inserted stent remains in the vessel after anastomosis formation is complete. In this case substantially cylindrical transplants made of metal, plastic or the like are connected by way of likewise cylindrical elements to the ends of the hollow organs or vessels that are to be connected. Connection of the elements to the vessel wall can be brought about, for example, by means of high-frequency current or conventionally, by inserting stitches. This operation always leaves elements in the vessel, which in the case of blood vessels increases the risk of thrombosis. Although this risk can be reduced by applying coatings of heparin or thrombolytic substances, it can never be entirely excluded.

BRIEF SUMMARY OF THE INVENTION

The object of the present invention is to create a device as cited above by means of which rapidly formed, but also reliable and permanent anastomoses of biological hollow organs can be produced. In addition the device is intended to be constructed in the simplest and most economical manner, and to present no danger of rejection and involve the lowest possible risk of thrombosis, in the case of blood vessels. The disadvantages of the state of the art are to be avoided, or at least reduced.

According to the present invention there is provided a device for the production of anastomoses between first and second hollow organs comprising an inner sleeve to be mounted around the end of the first hollow organ such that the end can then be turned inside out to lie over the inner sleeve; an outer sleeve to be mounted around the end of the second hollow organ after the latter end has been arranged over the inside out end of the first hollow organ; the inner and outer sleeves each being made separable so that they can be removed after anastomosis formation has been completed and comprising electrically conductive materials that can be connected to an external current or voltage source so that a current or a voltage can be applied to the electrically conductive materials for the electrocoagulation of the hollow organs that are to be connected to one another. The problem posed in accordance with the invention is thus solved by the fact that the inner sleeve and the outer sleeve comprise electrically conductive materials that can be connected to an external current or voltage source in order to apply a current or a voltage to the contact surfaces, so as to induce electrocoagulation of the hollow organs that are to be connected. The device in accordance with the invention combines the advantages of employing removable accessories for producing anastomoses, i.e. objects that are eliminated when the process of anastomosis has been completed, with a tissue bonding induced by electrocoagulation, which provides a particularly gentle but also secure and permanent connection of the hollow organs. The term "sleeve" denotes tubular as well as ring-shaped elements, which are positioned around the hollow organs that are to be connected and are as closely apposed thereto as possible. By means of the device described here, anastomoses can be produced without leaving any foreign bodies in place. As a result, in the case of blood vessels the risk of thrombosis is considerably reduced. It is possible for the inner and/or the outer sleeve to be made of the electrically conductive material itself. In this case, for instance, stainless steel or platinum can be used as electrically conductive material or as a coating of the sleeve, in particular where insertion into humans is concerned. It is also possible to dispose on the outer surface of the inner sleeve and/or the inner surface of the outer sleeve at least one contact surface made of electrically conductive material.

In this arrangement, the contact surfaces are preferably provided with suitable connecting wires, to provide a connection to the external current or voltage sources.

In order to achieve an annular fusion seam with no gaps, the contact surfaces on the inner sleeve and the outer sleeve are preferably circumferentially arranged. To improve the connection between the hollow organs, it is also possible for several circumferential contact surfaces to be disposed on the inner and outer sleeves, or else there can be a single, broad contact surface on the inner sleeve and several narrow contact surfaces on the outer sleeve.

The separability of the inner and/or outer sleeve can be implemented, according to another characteristic of the invention, by means of preferably spring-loaded pivotable parts. This can be achieved by an articulated linkage between the two sleeve parts or by disposing the sleeve parts on forceps- or clamp-like instruments, as is known per se, or by similar means.

The sleeve parts can comprise catch elements that can become interlocked when in the closed position, in order to provide a solid, continuous sleeve during the period of anastomosis formation.

The separability of the sleeves can also be achieved by providing predetermined breaking sites at which they can be broken apart when anastomosis formation is complete, so that the sleeves can be removed from the connected hollow organs, leaving the tissue junction free of foreign bodies. The breaking sites can be formed by axial grooves along the sleeves, which reduce the thickness of the material and make it easy to break the sleeve open. Similarly, the breaking sites can take the form of readily separable adhesive joints. In particular the outer sleeve can be formed in an especially simple manner by a wire arranged in the form of a loop, which is closely apposed to the outer surface of the hollow organs to be connected and by way of which an electrocoagulation current is imposed. Such a wire loop is also particularly easy to adjust to the circumference of the particular hollow organs to be connected. By providing the inner sleeve with fitting elements and the outer sleeve with elements having a complementary configuration, so that the two sets of elements can be fitted into one another during coagulation, it is possible to arrange the two sleeves in an orderly manner, so as to produce an orderly fusion of the hollow organs. Fitting elements of this kind can be formed by circumferential grooves on the sleeves.

The inner and/or outer sleeve can be made of plastic, for example polyethylene. This material is especially suitable for the cited purposes.

As mentioned above, the contact surfaces of the sleeves can consist of stainless steel or also of platinum.

In order to obtain information about the effect of the electrocoagulation, an impedance-measuring device can be disposed between the contact surfaces of the sleeves. By measuring the tissue impedance, the fusion of the hollow organs can be suitably monitored.

Information about the quality of coagulation can also be obtained by way of a temperature sensor disposed at the inner sleeve and/or the outer sleeve; thus the occurrence of unacceptably high tissue temperatures that might, for example, cause the cells to be destroyed, is indicated and can subsequently be prevented.

For the purpose of controlling the current or voltage introduced by way of the inner or outer sleeve, the current or voltage source can be connected to a control means.

In order to control the electrocoagulation time, the control means can comprise a timer that specifies the duration of the current or voltage pulse during the electrocoagulation process.

To construct a control circuit the impedance-measuring device and/or the temperature sensor can be connected to the current or voltage source or to a control means, if present, so that the process of hollow-organ fusion can take place under precisely prescribed conditions.

Since most hollow organs that need to be connected have a substantially cylindrical cross section, the sleeves are also substantially cylindrical in cross section. Naturally, a differently shaped cross section is likewise possible for special applications.

The present invention will now be explained further with reference to preferred exemplary embodiments and to the drawings, as follows.

DETAILED DESCRIPTION OF THE INVENTION

Figure 1:
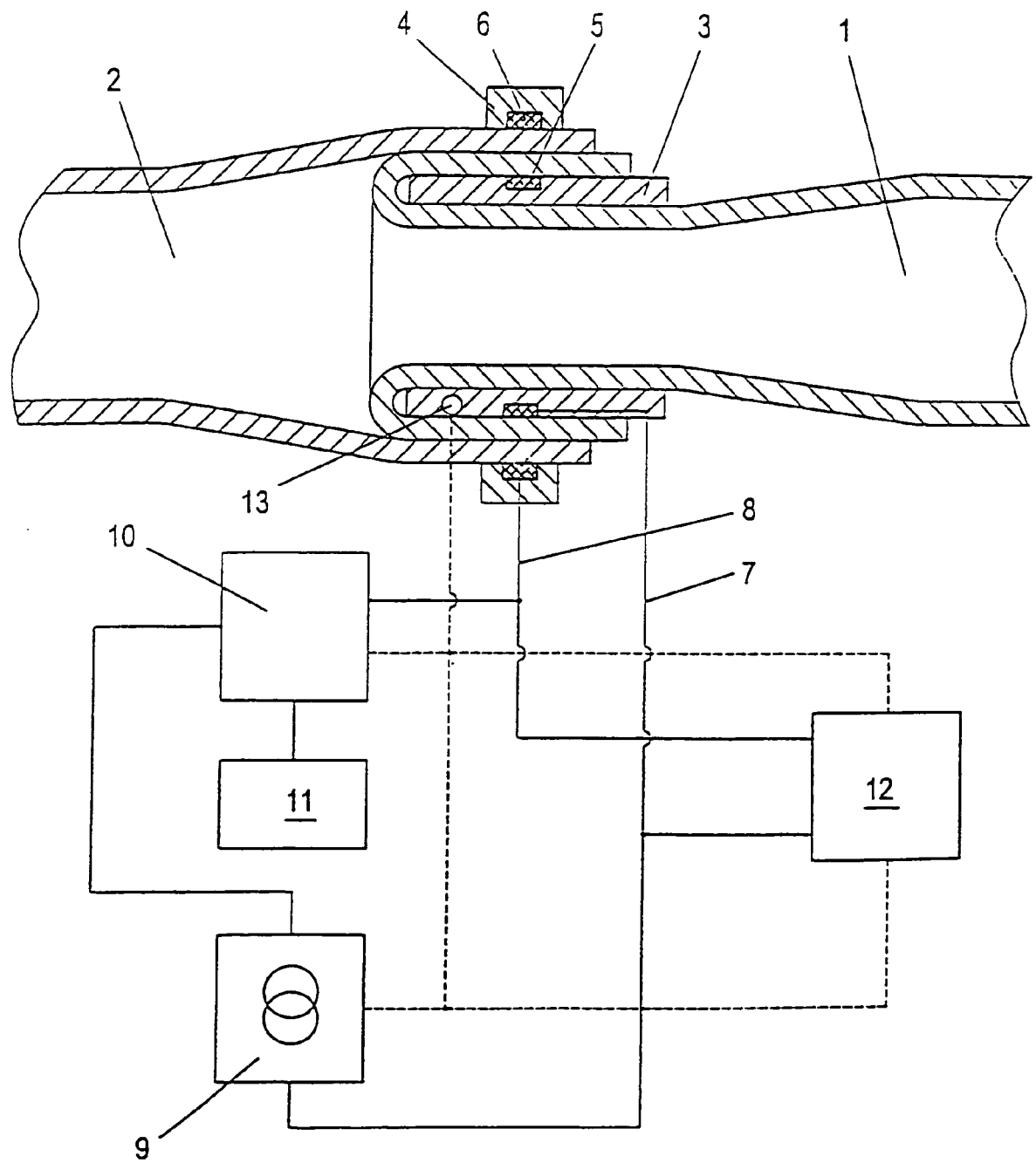
FIG. 1 shows a cross section through an end-to-end anastomosis for which the device in accordance with the invention is being used.

FIG. 1 shows a cross section through an end-to-end anastomosis of two hollow organs 1, 2, for example two arteries. Over the end of the hollow organ 1 a sleeve 3 has been pushed, and the end of the hollow organ 1 has been folded back over this sleeve 3. Then the end of the hollow organ 2 to be connected thereto is pushed over the inverted end of the first hollow organ 1, which now encloses the inner sleeve 3, and finally the outer sleeve 4 is placed over the inner sleeve 3. So that the sleeves 3, 4 can be removed after anastomosis is complete, each is designed to be separable. In accordance with the invention the inner sleeve 3 and the outer sleeve 4 both incorporate electrically conductive material, which preferably takes the form of corresponding contact surfaces 5, 6 in the sleeves 3, 4. It is likewise possible for the sleeves 3, 4 as a whole to be made of electrically conductive material. The contact surfaces 5, 6 are preferably disposed circumferentially around the sleeves 3, 4, so that after coagulation has been completed a continuous, secure connection between the hollow organs 1 and 2 will be achieved. In the example provided, the contact surfaces 5, 6 do not extend along an entire length of the inner and outer sleeves, respectively. The contact surfaces 5, 6 are connected by way of corresponding leads 7, 8 to an external current or voltage source 9, which applies an appropriate current or voltage to the contact surfaces 5, 6 for electrocoagulation of the hollow organs 1, 2 that are to be connected. Tc control the applied current or voltage, a control means 10 can be disposed between the current or voltage source 9 and the contact surfaces 5, 6 on the sleeves 3, 4, which can also include a time-switch 11 to determine the duration of the current or voltage pulses, or can be connected to such a time-switch 11. For measurement of the impedance of the tissue between the contact surfaces 5, 6 there can be connected to the leads 7, 8 a corresponding impedance-measuring apparatus 12, which in turn can be connected to the current or voltage source 9 or to the control device 10 to control the current or the voltage during the electrocoagulation. To monitor the temperature during electrocoagulation, in the inner sleeve 3 and/or the outer sleeve 4 can be disposed a temperature sensor 13, which is preferably connected directly to the current or voltage source 9 or to the control means 10 for regulating the connection process. With the device in accordance with the invention it is possible to create an optimal connection by employing the sleeves 3, 4 (which are known per se) and using electrical energy to fuse the tissues of the hollow organs 1, 2. After the anastomosis has been completed the sleeves 3, 4 are removed, so that no foreign bodies remain and a seamless connection between the hollow organs 1, 2 results.

Figure 2:
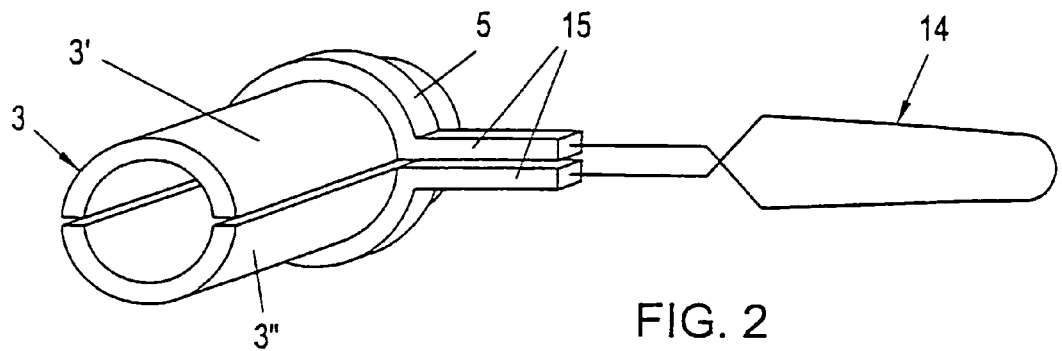
FIG. 2 is a perspective view of an embodiment of the inner sleeve.

FIG. 2 shows in perspective an inner sleeve 3 consisting of two pivotable components 3', 3" that are connected to the ends of a correspondingly shaped clamp 14 made of spring-steel wire. By pressing on the limbs of the clamp 14, the components 3' and 3" of the sleeve can be swiveled apart, and the sleeve 3 can be placed over the hollow organ 1 and, after anastomosis formation is complete, removed again. Here the clamp 14 makes electrically conductive connection with the contact surface 5 of the sleeve 3, by way of corresponding connector pieces 15, and the application of current is achieved directly by way of the clamp 14.

Figure 3:
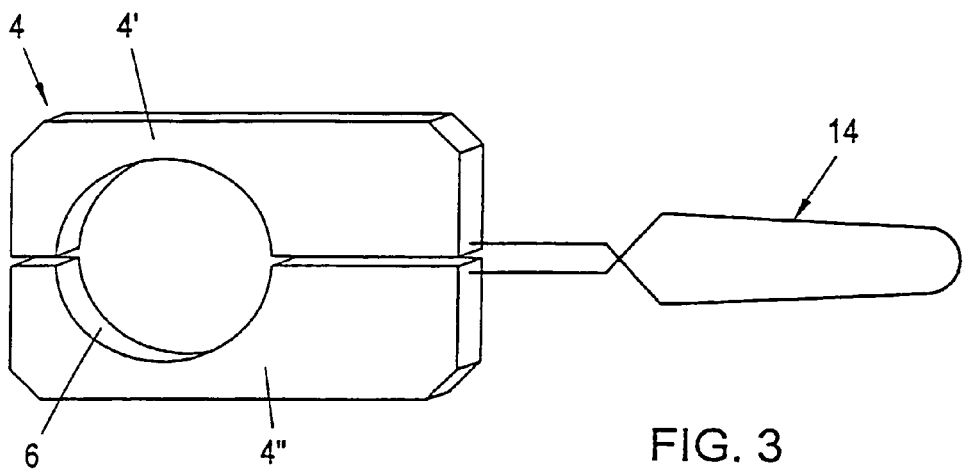
FIG. 3 is a perspective view of an embodiment of the outer sleeve.

FIG. 3 shows in perspective an embodiment of the outer sleeve 4 consisting of two parts 4', 4", which likewise are pivotably connected to one another by way of a clamp 14 made of spring-steel wire. Here, again, the contact surfaces 6 of the sleeve 4 are connected to the clamp 14 so as to be electrically conductive, and the connection to the current or voltage source 9 is implemented by way of the clamp 14.

Figure 4A:
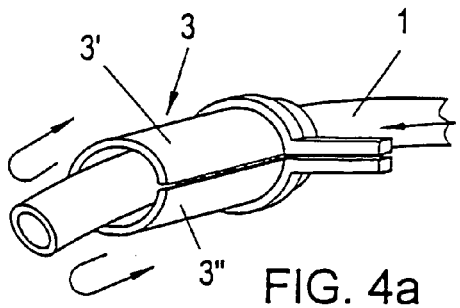
FIGS. 4a to 4h are perspective views of an end-to-end vascular anastomosis as it is being produced.
Figure 4B:
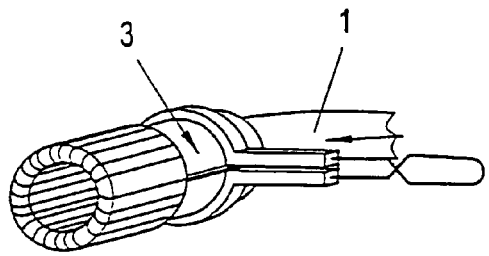
Figure 4C:
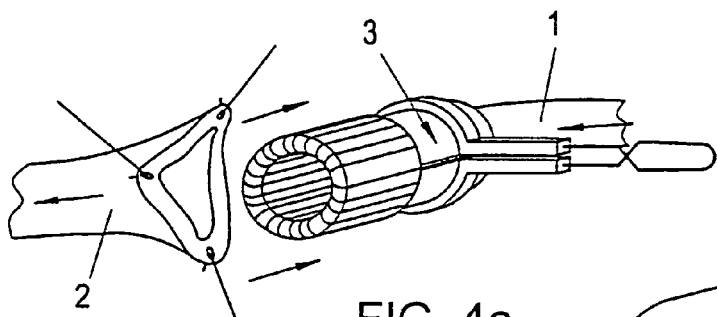
Figure 4D:
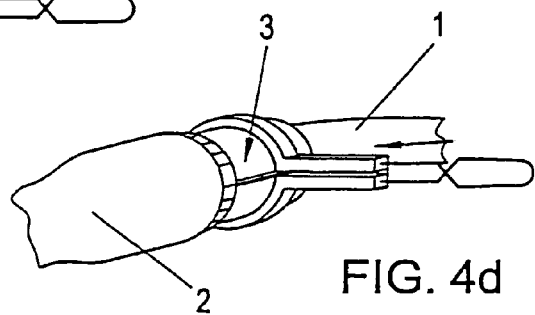
Figure 4E:
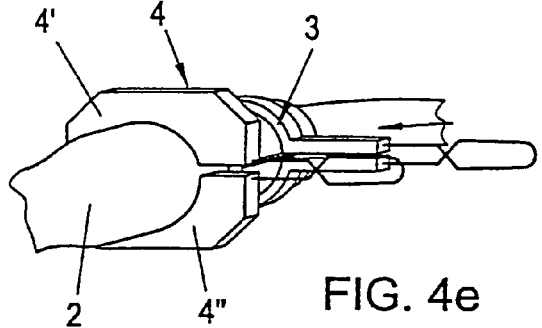
Figure 4F:
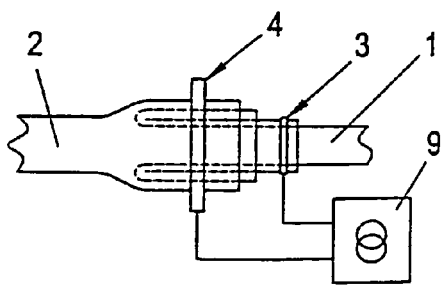
Figure 4G:
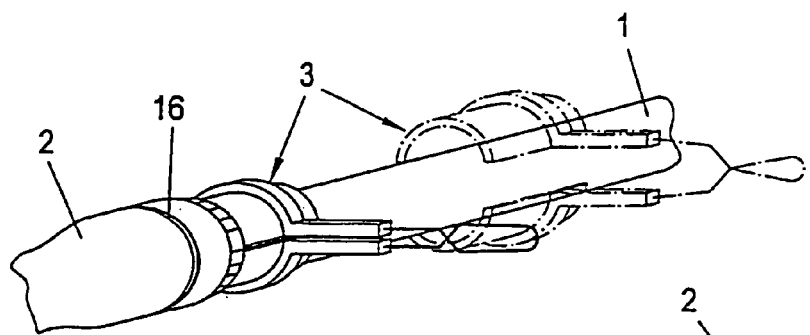
Figure 4H:
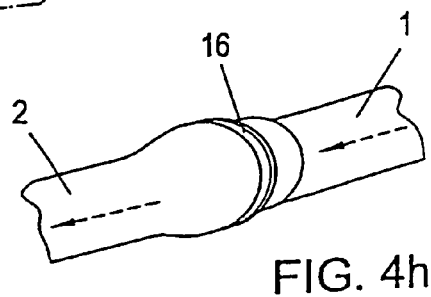

FIGS. 4a to 4h show the steps to be taken in creating an end-to-end anastomosis of two hollow organs 1, 2, such as blood vessels. In the first step the sleeve 3 is pushed over the end of the hollow organ 1, or else the parts 3', 3" of the sleeve 3 are rotated apart and, having been placed over the hollow organ 1 from the side, are closed again. As shown in FIG. 4b, the end of the hollow organ 1 is folded back over the sleeve 3. According to FIG. 4c the end of the second hollow organ 2 is pushed over the end of the first hollow organ 1, which has been inverted over the inner sleeve 3, so that the situation shown in FIG. 4d results. Thereafter, as shown in FIG. 4e, by rotation of the components 4' and 4" of the outer sleeve 4, the sleeve 4 is positioned axially so as to enclose the circumference of the hollow organ 2, overlying the sleeve 3. As shown in FIG. 4f, between the contact surfaces 5, 6 of the sleeves 3, 4 an electrical current or an electrical voltage with prespecified pulse shape, amplitude, duration and frequency is applied, as a result of which the cellular substance coagulates and brings about fusion of the protein structures comprising the tissue of the hollow organs 1 and 2. After removal of the outer sleeve 4, the resulting anastomosis is as shown in FIG. 4g, in which can be seen the resulting ring-shaped circumferential fusion seam 16. Thereafter the sleeve 3 is removed by first shifting it axially and then separating the components 3' and 3". The end result is an anastomosis as shown in FIG. 4h, which is free of all the accessories used during the formation of the anastomosis. The arrows in the hollow organs 1 and 2 indicate, for example in the case of a blood vessel, the possible direction of blood flow.

Figure 5A:
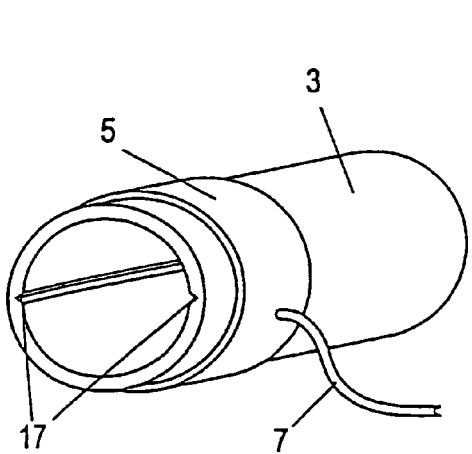
FIGS. 5a and 5b show an embodiment of an inner sleeve prior to use and after separation.
Figure 5B:
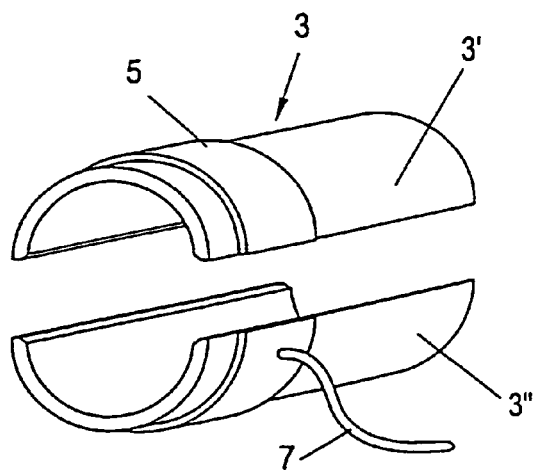

FIGS. 5a and 5b show an embodiment of an inner sleeve 3 with an annular contact surface 5, which is connected to an electrical supply cable 7. The sleeve 3 has on its inner surface predefined breaking sites 17 in the form of axially oriented grooves, which allow the sleeve 3 to be broken apart after the anastomosis is completed, so that the two separated components 3', 3" can be removed from the hollow organ 1 (FIG. 5b). Instead of such predefined breaking sites 17 it is possible for two initially separate components 3', 3" of the sleeve 3 to be glued together and subsequently separated.

Figure 6:
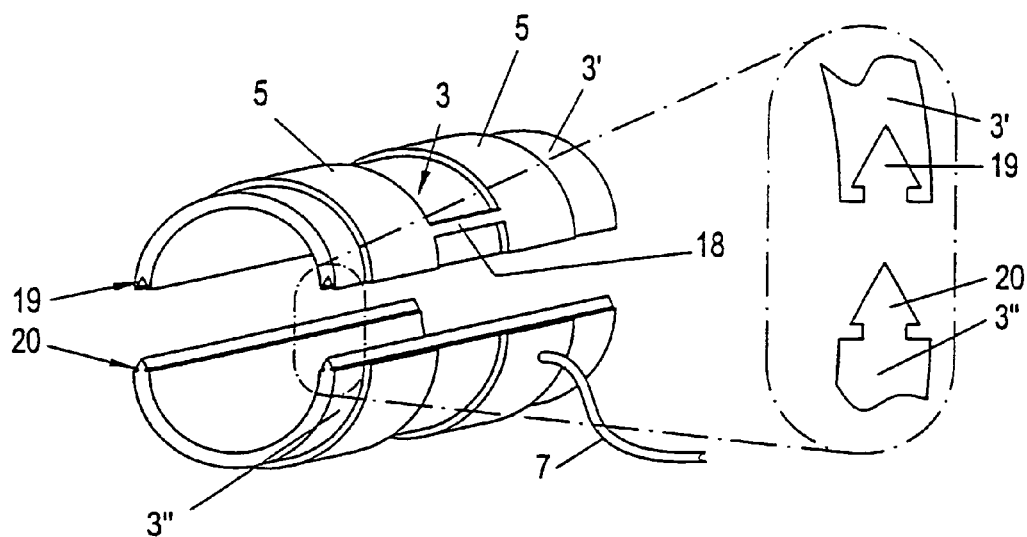
FIG. 6 is a perspective view of another embodiment of an inner sleeve.

FIG. 6 shows another embodiment of a sleeve 3, in which two annular contact surfaces 5 are electrically connected to one another by way of appropriate connecting elements 18. The components 3', 3" of the sleeve 3 can additionally be provided with catch elements 19, 20 that hold the components 3', 3" together when the sleeve 3 is in the closed position, but nevertheless make it possible for the components 3', 3" to be easily separated.

Figure 7:
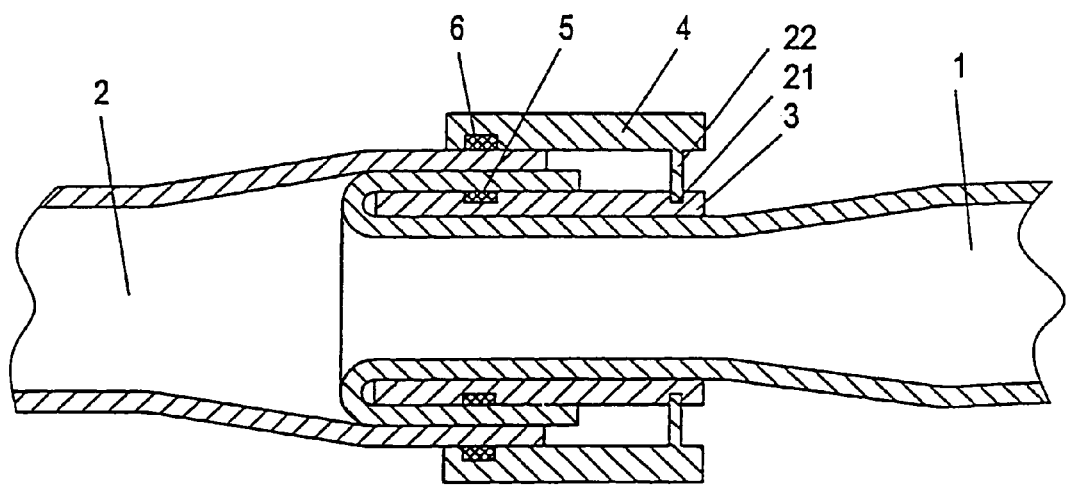
FIG. 7 shows a cross section through an end-to-end anastomosis for which another embodiment of the device in accordance with the invention is being used.

FIG. 7, finally, shows another embodiment of the device in accordance with the invention in cross section; in this case fitting elements 21, for example in the form of a circumferential groove, are disposed on the inner sleeve 3, and the outer sleeve 4 is provided with corresponding fitting elements 22 with a complementary shape, for example a likewise circumferential tongue, which enable exact positioning of the sleeves 3, 4 with respect to one another.

The invention is not restricted to the exemplary embodiments presented here, and can be modified within the scope of the claims.

The invention claimed is:

1. A removable electrocoagulative anastomosis device for the production of an electrocoagulated anastomosis between first and second hollow organs, the device comprising:
an inner sleeve constructed to be mounted around an end of the first hollow organ such that the end of the first hollow organ can then be turned inside out to lie over an end portion of the inner sleeve; and
an outer sleeve constructed to be mounted around an end of the second hollow organ after the end of the second hollow organ has been arranged over the inside out end of the first hollow organ, wherein
each of the inner and outer sleeves comprises two components and is separable or openable such that the inner and outer sleeves can be removed from the first and second hollow organs after formation of the electrocoagulated anastomosis is complete,
each of the inner and outer sleeves comprises an electrical connector coupled to electrically conductive material, wherein the inner sleeve comprises two annular contact surfaces which are electrically connected to one another by way of connecting elements, wherein one of the annular contact surfaces is connected to the electrical connector, and
wherein the electrical connectors of the inner and outer sleeves can be connected to an external current or voltage source so that a current or a voltage can be applied to the electrically conductive material of the inner and outer sleeves to form the electrocoagulated anastomosis, and
an outer circumference of the entire end portion of the inner sleeve over which the first hollow organ lies is smooth.

2. The device according to claim 1, wherein at least one of the inner sleeve and the outer sleeve is made substantially of the electrically conductive material.

3. The device according to claim 1, wherein at least one contact surface made of electrically conductive material is disposed at least one of the outer surface of the inner sleeve and the inner surface of the outer sleeve.

4. The device according to claim 3, wherein the contact surfaces on the inner sleeve and the outer sleeve are arranged circumferentially.

5. The device according to claim 1, wherein the outer sleeve is formed by a wire arranged in the shape of a loop.

6. The device according to claim 1, wherein the inner sleeve comprises fitting elements and the outer sleeve comprises fitting elements of complementary shape, which fit into one another in the arrangement used during electrocoagulation.

7. The device according to claim 1, wherein a portion of at least one of the inner sleeve and the outer sleeve is made of a plastics material.

8. The device according to claim 1, wherein each of the inner and outer sleeves comprises a contact surface made of stainless steel.

9. The device according claim 1, wherein an apparatus is provided to measure the impedance between the contact surfaces of the sleeves.

10. The device according to claim 9, wherein the apparatus is connected to one of the current source, the voltage source, and a control means connected to one of the current source and the voltage source.

11. The device according to claim 1, wherein a temperature sensor is disposed on at least one of the inner sleeve and the outer sleeve.

12. The device according to claim 11, wherein the temperature sensor is connected to one of the current source, the voltage source, and a control means connected to one of the current source and the voltage source.

13. The device according to claim 1, wherein a control means is connected to one of the current source and the voltage source.

14. The device according to claim 13, wherein the control means comprises a time-switch.

15. The device according to claim 1, wherein the sleeves have a substantially cylindrical cross section.

16. A removable electrocoagulative anastomosis system for production of electrocoagulated anastomoses between hollow organs, comprising:
an inner sleeve comprising a substantially tubular end portion, said inner sleeve constructed to be positioned around a first hollow organ proximate an end of said first hollow organ such that said end can then be everted over an outer circumferential portion of said substantially tubular end portion of said inner sleeve;
an outer sleeve constructed to be positioned around and to substantially enclose an outer circumference of a second hollow organ that has been pushed over both said inner sleeve and said everted end of said first hollow organ, wherein
said inner sleeve comprises two annular contact surfaces which are electrically connected to one another by way of connecting elements, wherein one of the annular contact surfaces is connected to the electrical connector,
said inner sleeve comprises an inner sleeve electrically conductive portion that extends substantially entirely around said outer circumference of said inner sleeve and an inner sleeve electrical connector,
said outer sleeve comprises an outer sleeve electrically conductive portion that extends substantially entirely around an inner circumference of said outer sleeve and an outer sleeve electrical connector,
each of said inner and outer sleeves is openable or separable in a fashion that permits removal of said sleeves from said first and second hollow organs after completion of an electrocoagulated anastomosis, and
said outer circumference of said substantially tubular end portion is smooth.

17. The system of claim 16, wherein said inner circumference of said outer sleeve is smooth.

18. The system of claim 16, comprising a regulated current or voltage source connected to said electrically conductive portion of said inner sleeve and said electrically conductive portion of said outer sleeve for effecting electrocoagulative anastomosis of said first and second hollow organs.

19. The system of claim 16, wherein said inner sleeve is made substantially of an electrically conductive material.

20. The system of claim 16, wherein
said inner sleeve, excepting said inner sleeve electrically conductive portion, is made substantially of a non-electrically conductive material, and
said inner sleeve electrically conductive portion comprises an electrically conductive contact surface at and extending substantially entirely around said outer circumferential portion of said substantially tubular end portion.

21. The system of claim 16, wherein said outer sleeve is made substantially of an electrically conductive material.

22. The system of claim 16, wherein
said outer sleeve, excepting said outer sleeve electrically conductive portion, is made substantially of a non-electrically conductive material, and
said outer sleeve electrically conductive portion comprises an electrically conductive contact surface at and extending substantially entirely around an inner circumference of said outer sleeve.

23. The system of claim 16, wherein said inner sleeve electrically conductive portion does not extend along an entire length of said inner sleeve.

24. The system of claim 16, wherein said outer sleeve electrically conductive portion does not extend along an entire length of said outer sleeve.

25. A removable electrocoagulative anastomosis system for production of electrocoagulated anastomoses between hollow organs, comprising:
an inner sleeve constructed to be positioned around a first hollow organ proximate an end of said first hollow organ such that said end can then be everted over an outer circumferential portion of said inner sleeve;
an outer sleeve constructed to be positioned around and to substantially enclose an outer circumference of a second hollow organ that has been pushed over said inner sleeve and said everted end of said first hollow organ, wherein
said inner sleeve comprises an inner sleeve body made substantially of a first material and an inner sleeve electrically conductive contact surface made substantially of a second material that differs from said first material, said inner sleeve electrically conductive contact surface being provided on said outer circumferential portion of said inner sleeve, forming at least one closed surface substantially entirely around said outer circumferential portion of said inner sleeve and extending in a longitudinal direction of said inner sleeve for a length that is less than a length of said inner sleeve in said longitudinal direction, said inner sleeve further comprises an inner sleeve electrical connector coupled to the inner sleeve electrically conductive contact surface, and said inner sleeve further comprises two annular contact surfaces which are electrically connected to one another by way of connecting elements, wherein an annular contact surface is connected to the electrical connector,
said outer sleeve comprises an outer sleeve electrically conductive contact surface on an inner circumference of said outer sleeve and an outer sleeve electrical connector coupled to the outer sleeve electrically conductive contact surface, said outer sleeve electrically conductive contact surface forming at least one closed surface entirely around said inner circumference of said outer sleeve, and
each of said inner and outer sleeves is openable or separable in a fashion that permits removal of said sleeves from said first and second hollow organs after completion of said electrocoagulated anastomoses.

26. A removable electrocoagulative anastomosis system for production of electrocoagulated anastomoses between hollow organs, comprising:
an inner sleeve constructed to be positioned around a first hollow organ proximate an end of said first hollow organ such that said end can then be everted over an outer circumferential portion of said inner sleeve;
an outer sleeve constructed to be positioned around and to substantially enclose an outer circumference of a second hollow organ that has been pushed over said inner sleeve and said everted end of said first hollow organ, wherein
said inner sleeve comprises an inner sleeve electrically conductive contact surface provided on said outer circumferential portion of said inner sleeve and an inner sleeve electrical connector coupled to the inner sleeve electrically conductive contact surface and the inner sleeve electrically conductive contact surface forming at least one closed surface substantially entirely around said outer circumferential portion of said inner sleeve,
said inner sleeve further comprises two annular contact surfaces which are electrically connected to one another by way of connecting elements, wherein one of the annular contact surfaces is connected to the electrical connector,
said outer sleeve comprises an outer sleeve body made substantially of a first material and an outer sleeve electrically conductive contact surface made substantially of a second material that differs from said first material, said outer sleeve electrically conductive contact surface being provided on an inner circumference of said outer sleeve, forming at least one closed surface substantially entirely around said inner circumference of said outer sleeve and extending in a longitudinal direction of said outer sleeve for a length that is less than a length of said outer sleeve in said longitudinal direction, said outer sleeve further comprises an outer sleeve electrical connector coupled to the outer sleeve electrically conductive contact surface, and
each of said inner and outer sleeves is openable or separable in a fashion that permits removal of said sleeves from said first and second hollow organs after completion of said electrocoagulated anastomoses.

* * * * *